United States Patent
Tayler

Patent Number: 5,665,750
Date of Patent: Sep. 9, 1997

[54] SYNERGISTIC FUNGICIDAL DIFENZOQUAT COMPOSITIONS

[75] Inventor: Peter Nigel Tayler, Hampshire, England

[73] Assignee: American Cyanamid Company, Parsippany, N.J.

[21] Appl. No.: 459,153

[22] Filed: Jun. 2, 1995

[30] Foreign Application Priority Data

Nov. 7, 1994 [GB] United Kingdom ............ 9422243

[51] Int. Cl.$^6$ ............ A01N 43/56; A01N 43/64
[52] U.S. Cl. ............................. 514/383; 514/406
[58] Field of Search ........................ 514/406, 383

[56] References Cited

U.S. PATENT DOCUMENTS

| | | | |
|---|---|---|---|
| 3,930,011 | 12/1975 | Walworth | 424/273 |
| 5,470,869 | 11/1995 | Tayler et al. | 514/406 |
| 5,476,868 | 12/1995 | Wingert et al. | 514/383 |

FOREIGN PATENT DOCUMENTS

| | | |
|---|---|---|
| 2119653 | 11/1983 | United Kingdom . |
| 2264641 | 9/1993 | United Kingdom . |

*Primary Examiner*—Allen J. Robinson
*Attorney, Agent, or Firm*—Gregory M. Hill

[57] ABSTRACT

There are provided methods for the control of phytopathogenic fungi, the control and prevention of disease caused thereby and the protection of crops therefrom. There is further provided a synergistic combination composition comprising 1,2-dimethyl-3,5-diphenylpyrazolium methyl sulfate and a sterol biosynthesis inhibitor.

11 Claims, No Drawings

SYNERGISTIC FUNGICIDAL DIFENZOQUAT COMPOSITIONS

BACKGROUND OF THE INVENTION

Safe, abundant, high quality food is the standard consumers demand. Food production relies on a variety of agricultural technologies to ensure the growing population's dietary needs remain affordable, nutritious and readily available on grocery store shelves. Fungicides are one of these agricultural technologies which are available to the world community. Fungicides are agrochemical compounds which shield crops and foods from fungus and fungal diseases. Crops and food are constantly threatened by a variety of fungal organisms, which if left uncontrolled can cause ruined crops and devastated harvests. Although the sterol biosynthesis inhibitors are among the most effective fungicides available, the level of control of *Erysiphe graminis* achieved by said fungicides in current cereal crop production is variable and often no greater than 60%.

Therefore, new fungicidal methods and compositions are needed to provide improved control of, and protection from, phytopathogenic fungal disease.

It is an object of this invention to provide a method of synergistic fungal control which will effectively improve the performance of sterol biosynthesis inhibitor fungicides for the control of powdery mildew in cereal crop production.

It is another object of this invention to provide an improved method of cereal crop protection against the ravages of powdery mildew infection and disease.

It is a further object of this invention to provide synergistic fungicidal compositions which are useful for improved control of mildew disease in cereal crop production.

SUMMARY OF THE INVENTION

The present invention provides a method for the control of a phytopathogenic fungus and the prevention or control of disease caused thereby which comprises contacting said fungus with a synergistically effective amount of a combination of 1,2-dimethyl-3,5-diphenylpyrazolium methyl sulfate (difenzoquat) and a sterol biosynthesis inhibitor wherein the said pyrazolium methyl sulfate and sterol biosynthesis inhibitor are present in a weight/weight ratio of about 0.10:1 to 15:1.

The present invention further provides improved crop protection methods and synergistic fungicidal compositions.

DETAILED DESCRIPTION OF THE INVENTION

Sterol biosynthesis inhibitors such as triazoles, morpholines, imidazoles, pyridines, piperidines, piperazines, pyrimidines and the like have a common biochemical target in fungal metabolism. Although the sterol biosynthesis inhibitors (SBI) are the most effective fungicides currently available, their ability to control powdery mildew in cereals is variable, often in the 60% or less range.

Surprisingly, it has been found that combinations of sterol biosynthesis inhibitors, preferably triazoles and morpholines, and 1,2-dimethyl-3,5-diphenylpyrazolium methyl sulfate (difenzoquat) give synergistic control of phytopathogenic fungal disease under both curative and prophylactic conditions. In particular, combinations of difenzoquat and triazoles such as fluotrimazole, triadimefon, triadimenol, hexaconazole, propiconazole, etaconazole, penconazole, flutriafol, epoxiconazole, flusilazole, diniconazole, tebuconazole, fenbuconazole, bromuconazole, difenconazole, tetraconazole, metconazole and the like or combinations of defenzoquat and morpholines such as fenpropimorph, tridemorph, fenpropidin, aldimorph and the like are synergistically effective for the control of powdery mildew in cereals such as oats, rye, triticale, wheat, barley and the like, especially wheat and barley.

In general, SBI fungicides such as triazoles and morpholines are commercially available for example as liquid or gel formulations and may be tank-mixed with difenzoquat prior to application. Alternatively, compositions comprising difenzoquat and a SBI fungicide in a weight/weight ratio of about 0.10:1 to 15:1 and an inert solid or liquid diluent may be used, preferably a synergistic fungicidal composition comprising difenzoquat and a triazole or morpholine compound in a weight/weight ratio of 0.10:1 to 15:1 and an inert liquid diluent. More preferred compositions are those having a combination of difenzoquat and a morpholine compound present at a weight/weight ratio of about 0.25:1 to 2:1 or a combination of difenzoquat and a triazole compound present at a weight/weight ratio of about 1:1 to 4:1. While not required, the combination composition of the invention may also contain other additives such as fertilizers, inert formulation aids, i.e. sufactants, emulsifiers, defoamers, dyes, extenders and the like.

Compositions according to the invention may be formulated in any conventional form, for example in the form of a twin pack, or as an emulsifiable concentrate, soluble concentrate, microemulsion, wettable powder, dispersible granular, soluble granular and the like.

In actual practice, a tank mix of a commercially convenient association or presentation of the SBI fungicide and difenzoquat may be applied to the foliage of the crop, or the SBI fungicide and difenzoquat may be applied separately or sequentially, or the combination compositions of the invention may be applied in a single combined form as described hereinabove. Rates of application of the combination or combination composition will vary according to prevailing conditions such as the particular SBI ingredient, the pathogenic fungi, degree of infestation, weather conditions, soil conditions, crop species, mode of application, application time and the like. However, rates of about 0.10 kg/ha to 1.0 kg/ha, preferably about 0.3 kg/ha to 0.5 kg/ha are suitable for a synergistic fungicidal effect. In general, the difenzoquat may be present in the combination at a weight/weight ratio of about 0.1:1 to 15:1 of difenzoquat to SBI fungicide, preferably about 0.25:1 to 4:1.

The synergistic combination compositions of the invention allow for effective resistance management programs in cereal crop production and offer better control of powdery mildew than can currently be achieved.

For a more clear understanding of the invention, specific examples thereof are set forth below. These examples are merely illustrative, and are not to be understood as limiting the scope and underlying principles of the invention in any way.

EXAMPLE 1

EVALUATION OF THE SYNERGISTIC EFFECT OF COMBINATIONS OF DIFENZOQUAT AND A STEROL BIOSYNTHESIS INHIBITOR ON PHYTOPATHOGENIC FUNGI UNDER PROPHYLACTIC CONDITIONS

Test plants are cultivated in the greenhouse in 6 cm diameter pots containing Fruhstorfer soil (type P). Eight to ten seeds are sown per pot and allowed to grow for one week prior to application of compounds.

A 10 mg sample of difenzoquat is added to 2.5 mL of demineralized water containing 0.0125 mL of acetone and 0.000625 mL of a surfactant, TRITON® X155, manufactured by Rohm and Haas, Philadelphia, Pa. This solution is further diluted with 61.5 mL of demineralized water to give a stock solution containing 100 ppm of difenzoquat. This stock solution is diluted with demineralized water as required for subsequent lower concentrations of active ingredient. Test compounds are evaluated alone or in tank mixtures. The mixtures are prepared no earlier than 0.5 hour before spraying. Test compounds are applied as foliar spray applications two days before inoculation.

For each treatment, four pots each containing eight to ten plants are sprayed in a spraying chamber using about 20 mL spray wash. After drying, the plants are returned to the greenhouse and maintained at 20° to 25° C.

Two days later the test plants are inoculated in the following manner: Barley or wheat stock culture plants vigorously infested and with heavily sporulating lesions of powdery mildew are shaken over the test plants until the leaves of the test plants are covered with a clearly visible dust of powdery mildew spores. Air movements are held to a minimum and the treated plants are maintained in the greenhouse at 21° to 28° C. for the duration of the experiment.

Six days after inoculation, the treated plants are evaluated for disease control as compared to a check (untreated plant). The percentage of leaf area infected of three individual leaves per pot is estimated. The % disease control of each treatment is determined using the formula shown below.

$$\% \text{ control} = 100 - \frac{\% \text{ level of disease of treated plant}}{\% \text{ level of disease of untreated plant}} \times 100$$

For all combinations, the expected value of disease control is calculated using Limpel's[1] formulas (a) and (b) shown below.

[1]Richer, D. L.: Synergism—A Patent View, Pesticide Science 19, 309–315 (1987)

$$E_a = X + Y \quad (a)$$

$$E_b = X + Y - \frac{XY}{100} \quad (b)$$

Formula (a) determines the expected value (i.e. additive effect) in all those cases wherein the expected value is ≦100%.

Formula (b) determines the expected value (i.e. additive effect) in all those cases wherein the expected value is >100%.

For both formula (a) and (b):

X=% disease control of difenzoquat alone;

Y=% disease control of the sterol biosynthesis inhibitor alone.

A synergistic effect is demonstrated when the observed value of the % disease control of a mixture (X+Y) is greater than the expected value of the mixture, as calculated by formula (a) or (b).

The results are shown in Table I.

| TEST COMPOUNDS | |
|---|---|
| Difenzoquat | (ACF-230 technical, American Cyanamid Co.) |
| Triadimenol | (BAYFIDAN ®, 250G/LEC, Bayer) |
| Tridemorph | (CALIXIN ®, 750g/LEC, BASF) |
| Fenpropimorph | (CORBEL ®, 750g/LEC, BASF) |
| Tebuconazole | (FOLICUR ®, 250g/LEC, Bayer) |
| Metconazole | (CARAMBA ®, 60g/LSL American Cyanamid Co.) |

| PATHOGENS |
|---|
| *Erysiphi graminis* f. sp. *tritici* |
| *Erysiphi graminis* f. sp. *hordei* |

The strains of *E. graminis* used in this experiment were not defined in terms of their sensibility to any of the above-listed chemical products. The strains are, therefore, characterized as undefined populations of "greenhouse strains" of *E. graminis*.

| TEST PLANTS | |
|---|---|
| Barley | *Hordeum vulgare*, c.v. Golden Promise |
| Wheat | *Triticum aestivum*, c.v. Kanzler |

TABLE I

PROPHYLACTIC EVALUATION OF TEST COMPOUNDS

| | | % Disease Control | | | |
|---|---|---|---|---|---|
| | | Barley | | Wheat | |
| Compound (mixture) | Dose (ppm) | Observed | Expected | Observed | Expected |
| Difenzoquat (A) | 6.3 | 0 | | 22 | |
| | 7.9 | 0 | | 28 | |
| | 12.6 | 5 | | 43 | |
| | 25.0 | 3 | | 35 | |
| | 31.3 | 32 | | 48 | |
| | 50.5 | 28 | | 95 | |
| | 106.3 | 99 | | 99 | |
| | 125 | 98 | | 98 | |
| Triadimenol (B) | 0.025 | 0 | | 0 | |
| | 0.1 | 0 | | 7 | |
| | 0.4 | 22 | | 38 | |
| | 25 | 100 | | 100 | |
| Tridemorph (C) | 6.3 | 0 | | 16 | |
| | 25 | 0 | | 11 | |
| | 50 | 28 | | 23 | |
| | 100 | 76 | | 16 | |
| | 125 | 98 | | 22 | |
| | 200 | 100 | | 91 | |
| Fenpropimorph (D) | 0.4 | 24 | | 23 | |
| | 1.6 | 32 | | 3 | |
| Fenpropimorph (D) | 6.3 | 99 | | 16 | |
| | 25 | 100 | | 50 | |
| | 100 | 100 | | 97 | |
| Tebuconazole (E) | 0.025 | 0 | | 10 | |
| | 0.1 | 12 | | 34 | |
| | 25 | 100 | | 100 | |
| Metconazole (F) | 0.1 | 0 | | 15 | |
| | 0.4 | 0 | | 16 | |

TABLE I-continued

PROPHYLACTIC EVALUATION OF TEST COMPOUNDS

| | % Disease Control | | | |
|---|---|---|---|---|
| | Barley | | Wheat | |
| | Observed | Expected | Observed | Expected |
| 1.6 | 18 | | 23 | |
| 25 | 100 | | 100 | |
| 100 | 100 | | 100 | |
| Mixture Dose (ppm) | | | | |
| A + B | | | | |
| 6.3 + 0.025 | 0 | 0 | 25 | 22 |
| 6.3 + 0.1 | 15+ | 0 | 18 | 29 |
| 6.3 + 0.4 | 11 | 22 | 23 | 60 |
| 25 + 0.025 | 21+ | 3 | 41+ | 35 |
| 25 + 0.1 | 13+ | 3 | 33 | 42 |
| 25 + 0.4 | 40+ | 25 | 87+ | 73 |
| A + C | | | | |
| 6.3 + 6.3 | 21+ | 0 | 54+ | 38 |
| 6.3 + 25 | 83+ | 0 | 53+ | 33 |
| 6.3 + 100 | 100+ | 76 | 65+ | 38 |
| 25 + 6.3 | 30+ | 3 | 56+ | 51 |
| 25 + 25 | 41+ | 3 | 90+ | 46 |
| 25 + 100 | 100+ | 79 | 96+ | 51 |
| A + D | | | | |
| 6.3 + 0.4 | 22 | 24 | 22 | 45 |
| 6.3 + 1.6 | 53+ | 32 | 33+ | 25 |
| 6.3 + 6.3 | 99 | 99 | 36 | 38 |
| 25 + 0.4 | 50+ | 27 | 50 | 58 |
| 25 + 1.6 | 87+ | 35 | 60+ | 38 |
| 25 + 6.3 | 100 | 99 | 76 | 51 |
| A + E | | | | |
| 6.3 + 0.025 | 13+ | 0 | 35 | 32 |
| 6.3 + 0.1 | 22+ | 12 | 40 | 56 |
| 25 + 0.025 | 21+ | 3 | 58+ | 45 |
| 25 + 0.1 | 61+ | 15 | 58 | 69 |
| A + F | | | | |
| 6.3 + 0.1 | 0 | 0 | 36 | 37 |
| 6.3 + 0.4 | 6+ | 0 | 12 | 38 |
| 6.3 + 1.6 | 28+ | 18 | 40 | 45 |
| 25 + 0.1 | 46+ | 3 | 64+ | 50 |
| 25 + 0.4 | 39+ | 3 | 64+ | 51 |
| 25 + 1.6 | 93+ | 21 | 75+ | 58 |
| Base value of infection on untreated plants | 100% | | 100% | |

+designates observed value > expected value

EXAMPLE 2

EVALUATION OF THE SYNERGISTIC EFFECT OF COMBINATIONS OF DIFENZOQUAT AND A STEROL BIOSYNTHESIS INHIBITOR ON PHYTOPATHOGENIC FUNGI UNDER CURATIVE CONDITIONS

Using essentially the same procedure described in Example 1, but inoculating the 7 day old plants first, then 2 days later treating the infected plants with spray applications of test compounds, the following results are obtained and shown in Table II.

TABLE II

CURATIVE EVALUATION OF TEST COMPOUNDS

| | | % Disease Control | | | |
|---|---|---|---|---|---|
| | | Barley | | Wheat | |
| Compound (Mixture) | Dose (ppm) | Observed | Expected | Observed | Expected |
| Difenzoquat (A) | 1.6 | 0 | | 0 | |
| | 6.3 | 0 | | 0 | |
| | 25.0 | 0 | | 0 | |
| | 50.0 | 0 | | 0 | |
| | 62.5 | 0 | | 25 | |
| | 75 | 3 | | 59 | |
| | 100 | 24 | | 68 | |
| Tridemorph (B) | 1.6 | 0 | | 0 | |
| | 6.3 | 0 | | 0 | |
| | 7.9 | 0 | | 0 | |
| | 12.5 | 8 | | 0 | |
| | 18.8 | 13 | | 0 | |
| | 25 | 23 | | 0 | |
| | 31.3 | 29 | | 9 | |
| | 37.5 | 51 | | 4 | |
| | 50 | 84 | | 7 | |
| (B) | 62.5 | 95 | | 33 | |
| | 75 | 100 | | 34 | |
| | 100 | 100 | | 93 | |
| Metconazole (C) | 0.4 | 0 | | 0 | |
| | 0.8 | 0 | | 11 | |
| | 1.6 | 12 | | 19 | |
| | 3.2 | 30 | | 33 | |
| | 4.8 | 69 | | 74 | |
| | 6.3 | 96 | | 94 | |
| | 9.5 | 97 | | 100 | |
| | 12.5 | 99 | | 100 | |
| | 18.8 | 100 | | 100 | |
| Mixture Dose (ppm) | | | | | |
| A + B | | | | | |
| 1.6 + 1.6 | | 0 | 0 | 0 | 0 |
| 1.6 + 6.3 | | 6+ | 0 | 4+ | 0 |
| 1.6 + 12.5 | | 21+ | 8 | 14+ | 0 |
| 1.6 + 25 | | 72+ | 23 | 28+ | 0 |
| 1.6 + 50 | | 90+ | 84 | 60+ | 7 |
| 6.3 + 1.6 | | 0 | 0 | 0 | 0 |
| 6.3 + 6.3 | | 0 | 0 | 0 | 0 |
| 6.3 + 12.5 | | 18+ | 8 | 7+ | 0 |
| 6.3 + 25 | | 74+ | 23 | 14+ | 0 |
| 6.3 + 50 | | 99+ | 84 | 48+ | 7 |
| 12.5 + 1.6 | | 3+ | 0 | 0 | 0 |
| 12.5 + 6.3 | | 17+ | 0 | 11+ | 0 |
| 12.5 + 12.5 | | 50+ | 8 | 15+ | 0 |
| A + B | | | | | |
| 12.5 + 25 | | 77+ | 23 | 67+ | 0 |
| 12.5 + 50 | | 92+ | 84 | 97+ | 7 |
| 25 + 1.6 | | 0 | 0 | 18+ | 0 |
| 25 + 6.3 | | 8+ | 0 | 36+ | 0 |
| 25 + 12.5 | | 78+ | 8 | 52+ | 0 |
| 25 + 25 | | 80+ | 23 | 78+ | 0 |
| 25 + 50 | | 90+ | 84 | 85+ | 7 |
| 50 + 1.6 | | 21+ | 0 | 4+ | 0 |
| 50 + 6.3 | | 43+ | 0 | 13+ | 0 |
| 50 + 12.5 | | 46+ | 8 | 30+ | 0 |
| 50 + 25 | | 85+ | 23 | 85+ | 0 |
| 50 + 50 | | 100+ | 84 | 95+ | 7 |
| A + C | | | | | |
| 1.6 + 0.4 | | 0 | 0 | 11 | 0 |
| 1.6 + 0.8 | | 0 | 0 | 15+ | 11 |
| 1.6 + 1.6 | | 5 | 12 | 29+ | 19 |
| 1.6 + 3.2 | | 24 | 30 | 79+ | 33 |
| 1.6 + 6.3 | | 97 | 96 | 98 | 94 |
| 6.3 + 0.4 | | 0 | 0 | 4 | 0 |

TABLE II-continued

CURATIVE EVALUATION OF TEST COMPOUNDS

| | % Disease Control | | | |
|---|---|---|---|---|
| | Barley | | Wheat | |
| | Observed | Expected | Observed | Expected |
| 6.3 + 0.8 | 0 | 0 | 13 | 11 |
| 6.3 + 1.6 | 28+ | 12 | 19 | 19 |
| 6.3 + 3.2 | 71+ | 30 | 57+ | 33 |
| 6.3 + 6.3 | 94 | 96 | 94 | 94 |
| 12.5 + 0.4 | 0 | 0 | 0 | 0 |
| 12.5 + 0.8 | 0 | 0 | 0 | 11 |
| 12.5 + 1.6 | 4 | 12 | 13 | 19 |
| A + C | | | | |
| 12.5 + 3.2 | 61+ | 30 | 74+ | 33 |
| 12.5 + 6.3 | 99 | 96 | 93 | 94 |
| 25 + 0.4 | 0 | 0 | 6+ | 0 |
| 25 + 0.8 | 0 | 0 | 11 | 11 |
| 25 + 1.6 | 28+ | 12 | 49+ | 19 |
| 25 + 3.2 | 94+ | 30 | 80+ | 33 |
| 25 + 6.3 | 98 | 96 | 95 | 94 |
| 50 + 0.4 | 0 | 0 | 8+ | 0 |
| 50 + 0.8 | 7 | 0 | 13 | 11 |
| 50 + 1.6 | 76+ | 12 | 25+ | 19 |
| 50 + 3.2 | 85+ | 30 | 92+ | 33 |
| 50 + 6.3 | 99 | 96 | 97 | 94 |
| Base value of infection on untreated plants | 100% | | 100% | |

+designates observed effect is > expected effect

EXAMPLE 3

EVALUATION OF THE EFFECT OF DIFENZOQUAT AND TRIAZOLE COMBINATIONS ON WHEAT POWDERY MILDEW UNDER FIELD CONDITIONS

In this test, treatments are applied to winter wheat (cv Riband) when flag leaves have fully emerged but are almost vertical. The stands of wheat show no mildew infection on the canopy or on the penultimate leaf, but do show visible infection on the F-3 leaf at the time of application. Interaction between difenzoquat and selected triazole fungicides in the control of wheat powdery mildew is investigated in a full factorial combination.

Commercial formulations of triazole fungicides and difenzoquat are used. Spray applications are made at 2.5 bar pressure through 110° fan jet nozzles using a custom designed field plot sprayer. Observations of powdery mildew infection (measured as pustules per F-3 leaf) are made at 0, 7, 21, 28 and 33 days after spraying. The % disease control is calculated using the following formula:

$$\% \text{ control} = 100 - \frac{\text{mean value of infection of treated plant}}{\text{mean value of infection of untreated plant}} \times 100$$

For all combinations, the expected value of disease control is calculated using Limpel's[1] formulas (a) and (b) shown below.

[1]Richer, D. L.: Synergism—A Patent View, Pesticide Science 19, 309–315 (1987)

$$E_a = X + Y \quad \text{(a)}$$

$$E_b = X + Y - \frac{XY}{100} \quad \text{(b)}$$

Formula (a) determines the expected value (i.e. additive effect) in all those cases wherein the expected value is ≦100%.

Formula (b) determines the expected value (i.e. additive effect) in all those cases wherein the expected value is >100%.

For both formula (a) and (b):
X=% disease control of difenzoquat alone
Y=% disease control of triazole alone A synergistic effect is demonstrated when the observed value of the % disease control of a mixture (X+Y) is greater than the expected value of the mixture as calculated by formula (a) or (b).

Evaluations of the upper canopy (prophylactic conditions) and of the F-3 leaves (curative conditions) are made.

The treatments appeared to have an additive effect on the upper canopy and a synergistic effect was observed on the lower leaves. The results of the evaluation of the F-3 leaf at 33 days after spraying are shown in Table III.

TEST COMPOUNDS

| Propiconazole | (RADAR ®, Zeneca) |
|---|---|
| Flusilazole | (GENIE ®, DuPont) |
| Tebuconazole | (FOLICUR ®, Bayer) |
| Difenzoquat | (American Cyanamid) |

TABLE III

FIELD EVALUATION OF TEST COMPOUNDS ON POWDERY MILDEW CONTROL ON WINTER WHEAT (F-3 LEAF) (CURATIVE CONDITIONS)

| | | % Disease Control | |
|---|---|---|---|
| Compound (Mixture) | Rate g/ha | Observed | Expected |
| Difenzoquat (A) | 200 | 14.6 | — |
| Propiconazole (B) | 125 | 29.3 | — |
| Flusilazole (C) | 160 | 26.8 | — |
| Tebuconazole (D) | 250 | 53.7 | — |
| Mixture Rate (g/ha) | | | |
| A + B (200 + 125) | | 77.0+ | 43.5 |
| A + C (200 + 160) | | 56.1+ | 41.4 |
| A + D (200 + 250) | | 75.6+ | 68.3 |
| Base value of infection on untreated wheat stands | | 100% | |

+designates observed value > expected value

I claim:

1. A method for the synergistic control of a phytopathogenic fungus and the prevention or control of disease caused thereby which comprises contacting said fungus with a synergistic fungicidally effective amount of a combination of difenzoquat and metconazole wherein said difenzoquat and metconazole are present in a weight ratio of about 0.10:1 to 15:1.

2. The method according to claim 1 wherein the fungus is of the genus Erysiphe.

3. The method according to claim 1 wherein the difenzoquat and metconazole are present in a ratio of about 0.25:1 to 4:1.

4. The method according to claim 2 wherein the fungus is *Erysiphe, graminis*.

5. A method for the protection of a cereal crop plant from fungal infestation and disease which comprises adding to the foliage of said plant a synergistic fungicidally effective amount of a combination of difenzoquat and metconazole wherein said difenzoquat and metconazole are present in a weight/weight ratio of about 0.10:1 to 15:1.

6. The method according to claim 5 wherein the cereal crop is wheat or barley.

7. The method according to claim 5 wherein the difenzoquat and metconazole are present in a ratio of about 0.25:1 to 4:1.

8. The method according to claim 6 wherein the fungus is of the genus Erysiphe.

9. A synergistic fungicidal composition which comprises difenzoquat and metconazole in a weight/weight ratio of about 0.1:1 to 15:1 and an inert solid or liquid diluent.

10. The composition according to claim 9 wherein the weight/weight ratio is about 0.25:1 to 4:1.

11. The composition according to claim 9 wherein the weight/weight ratio is about 1:1 to 4:1.

* * * * *